United States Patent
Las et al.

(10) Patent No.: US 9,364,001 B2
(45) Date of Patent: Jun. 14, 2016

(54) QUATERNARY FUNGICIDAL MIXTURE

(71) Applicant: ADAMA MAKHTESHIM LTD., Beer Sheva (IL)

(72) Inventors: Allan S. Las, Bellevue, WA (US); Jerry L. Corbett, Selma, NC (US); Paul R. Moore, Valdosta, GA (US)

(73) Assignee: ADAMA MAKHTESHIM LTD., Beer Sheva (IL)

( * ) Notice: Subject to any disclaimer, the term of this patent is extended or adjusted under 35 U.S.C. 154(b) by 24 days.

(21) Appl. No.: 14/458,486

(22) Filed: Aug. 13, 2014

(65) Prior Publication Data

US 2015/0126569 A1    May 7, 2015

Related U.S. Application Data

(60) Provisional application No. 61/901,178, filed on Nov. 7, 2013.

(51) Int. Cl.
| | |
|---|---|
| *A01N 37/34* | (2006.01) |
| *A01N 43/653* | (2006.01) |
| *A01N 47/38* | (2006.01) |
| *A01N 65/00* | (2009.01) |
| *A01N 47/34* | (2006.01) |
| *A01N 43/48* | (2006.01) |

(52) U.S. Cl.
CPC ............. *A01N 47/38* (2013.01); *A01N 37/34* (2013.01); *A01N 43/48* (2013.01); *A01N 43/653* (2013.01); *A01N 47/34* (2013.01); *A01N 65/00* (2013.01)

(58) Field of Classification Search
None
See application file for complete search history.

(56) References Cited

U.S. PATENT DOCUMENTS

| | | | |
|---|---|---|---|
| 5,240,952 A | 8/1993 | Brandes et al. | |
| 2010/0152270 A1* | 6/2010 | Suty-Heinze et al. | 514/414 |

FOREIGN PATENT DOCUMENTS

| | | |
|---|---|---|
| CN | 1233395 A | 11/1999 |
| CN | 1833503 A | 9/2006 |
| CN | 1947512 A | 4/2007 |
| CN | 101278678 A | 10/2008 |
| CN | 100477913 C | 4/2009 |
| CN | 101524078 B | 5/2012 |
| EP | 663148 A2 | 7/1995 |
| ES | 2115490 A1 | 6/1998 |
| JP | 57014647 A | 1/1982 |
| JP | 05320007 A | 12/1993 |
| RU | 2373711 C1 | 11/2009 |
| WO | 2007/009775 A2 | 1/2007 |

OTHER PUBLICATIONS

"Chlorothalonil Compositions"; Research Disclosure (2000), 438 (Oct.), p. 1752-p. 1755 (No. 438040).

\* cited by examiner

*Primary Examiner* — James D Anderson
*Assistant Examiner* — Meghan Finn
(74) *Attorney, Agent, or Firm* — Nath, Goldberg & Meyer; Joshua B. Goldberg

(57) ABSTRACT

A quaternary fungicide mixture for controlling diseases of turfgrass and/or ornamentals.

12 Claims, No Drawings

QUATERNARY FUNGICIDAL MIXTURE

FIELD OF THE PRESENT SUBJECT MATTER

The present subject matter relates to a quaternary fungicide mixture for controlling diseases of turfgrass and ornamentals.

BACKGROUND OF THE PRESENT SUBJECT MATTER

Turf and ornamental grasses are subject to various pathogenic fungi which affect them under different temperature regimes (−20 to 45° C.) in all seasons and even under snow cover. Control of phytopathogenic fungi such as dollar spot (*Sclerotinia homeocarpa*), brown patch (*Rhizoctonia solani*), foliar and basal Anthracnose (*Colletotrichum cereale*) in warm- and cool-season grasses, or snow molds (*Microdochium nivale, Typhula incarnata*, and *Typhula ishikariensis*) in regions and climates with long duration snow cover is particularly important in high-value turfgrass used for golf courses and sod farms.

Different commercial fungicides are known and used for treating these turf diseases. Known treatments comprise repeated applications of fungicides in-season to prevent or for curative efficacy of incipient lesions, to prevent premature senescence, bleaching, or blade death, and to improve green-up and turf quality before or after snow cover where snow cover is historically longer than 60 days. Researchers and experienced turfgrass managers have long come to realize that repeated applications of the same fungicide, or fungicides of the same class inhibiting a specific metabolic site, or fungicides from different classes but possessing the same biochemical mode of action, can promote rapid onset of resistance by the pathogen or promote other pathogens released from their normal competition such that whole categories of fungicides can be lost as effective agents of disease control.

More recently, golf superintendants, lawn care specialists and managers of turfgrass have learned to treat high-value turf in a programmatic way in which fungicides with different biochemical modes of action are rotated throughout the season in an effort to manage resistance. This requires end-users to procure and inventory several different fungicides, each with their own specific concentration and regulatory instructions, and to study each label in order to comply with EPA-approved use rates that provide effective control but prevent turfgrass injury due to improper sequencing of applications or over-treatment due to conflicting demands on treatment intervals imposed by each fungicide. Some fungicides require short re-treatment intervals, such as contact fungicides, while other fungicides with limited or fully systemic properties permit longer intervals between re-treatment. As a result, program spraying is often complex given the variety of use rates, treatment intervals, and whether or not a given fungicide works solely as a preventative or can be used to treat turf with existing lesions or other symptoms of infection.

Another approach has been to combine fungicides, typically with different biochemical modes of action, in one concentrate in an effort to forestall resistance, broaden the spectrum of control, and to obviate the need to inventory the many individual brands of fungicides otherwise necessary. Combinations of chlorothalonil (a contact nitrile)+propiconazole (a sterol biosynthesis inhibitor) exist, as does a combination of thiophanate methyl (a systemic benzimidazole)+iprodione (a dicarboximide with acropetal penetration of grass blades). In the prior art only two and three way mixtures of fungicides for foliar application are presently known. For example, U.S. Pat. No. 5,240,952 discloses a synergistic composition of tebuconazole with iprodione; US Patent Application Publication No. US 2008/0269174 discloses a combination of tebuconazole with chlorothalonil; and U.S. Pat. No. 8,377,850 discloses a synergistic composition, comprising: trifloxystrobin, iprodione, and phthalocyanine green pigment Green 7.

Chlorothalonil was first described by N. J. Turner et al. (Contrib. Boyce Thompson Inst., 1964, 22, 303).

Iprodione was first described by L. Lacroix et al. (Phytiatr. Phytopharm., 1974, 23, 165).

Thiophanate methyl was first described by K. Ishii (Abstr. Int. Congr. Plant Prot., 7th, Paris, 1970, p. 200).

Tebuconazole was first described by Kuck & Berg (Mitt. Biol. Bundesanstalt. Land.-Forstwirtsch. Berlin-Dahlem, 1986, 232, 196).

While these two-way fungicide combinations improve the convenience of addressing various turfgrass diseases using multiple modes of action or target sites they have been shown to not provide a complete solution to in-season or snow mold disease management. The recommended use rates of these combinations often burden the environment in applying as much total fungicide as tank-mixes of each individual fungicide. These combinations of fungicides or tank-mixes show additive effects at best but not more. A three-way fungicide combination is also known but it contains an active ingredient (a sterol biosynthesis inhibitor) well known to phase into layers on the shelf and display plant growth regulator effects, which when used repeatedly or under periods of high temperatures often reduces playability of greens due to turf-thinning. Accordingly, there remains a need in the art to develop an effective mixture and composition thereof which affects all season fungi and treats a broad spectrum of fungal diseases economically while lowering the chemical burden on the environment.

SUMMARY OF THE PRESENT SUBJECT MATTER

Surprisingly, a complete fungicide has now been found that combines preventative and curative fungicides, systemic, acropetal, and contact modes of action, in a complementary ratio. When applied repeatedly or in a program, the present mixture provides total control of an array of turfgrass diseases without causing turf-thinning or other symptoms of phytotoxicity, without imposing on practitioners of the art the need to add fractions of an ounce of individual fungicides per area treated, or the need to track re-treatment intervals based on which fungicide was applied before.

In addition, it has been discovered that the present quaternary fungicide mixture works at far lower rates of active ingredient than are applied when mixing individual chemicals at their approved use rates or when combinations previously available are used at labeled rates. This reduces the chemical burden on the environment. An additional advantage is that while efficacy of the present fungicide mixture is superior at lower overall use rates (per area treated), the duration of the protection conferred is not reduced.

The present quaternary fungicidal combination has excellent fungicidal activity against a broad spectrum of economically important basidiomycetes, ascomycetes, ETRI, and deuteromycetes pathogens. This combination contains a balanced ratio of contact to systemic to sterol biosynthesis inhibitor (SBI), and can be used repeatedly without causing turf-thinning. The all-in-one composition can be prepared as a stable, accurate-to-dilute concentrate, and is capable of maintaining the original, fixed ratio of each of the four fungicides it contains without undue variance for longer than one year under ambient conditions and for 4 weeks under accelerated storage conditions. Accordingly, this combination is classified by the EPA in the most user-friendly handling category, CAUTION, in marked contrast to a two-way mixture of chlorothalonil+propiconazole, which is listed as DANGER, or a two-way mixture of thiophanate methyl+iprodione, which carries a WARNING on its label.

Rates of application of the present combination are customized so that end-users can simply apply whole integers of fluid ounces (or for the metric system increments of 30 ml) to whichever unit measure of area is appropriate, for instance, per 1000 square feet (hereinafter abbreviated "per M"), per $100M^2$, per acre, or per hectare. For example, using the quaternary fungicidal mixture at 3 fl oz per M on a bi-weekly schedule, or for extended control 4 fl oz every 21-days, provides complete control while lessening the risk of exposing pathogens to sublethal dosages or repeated use of a single biochemical mode of action that would otherwise promote resistance.

Using the present quaternary fungicidal mixture, for example, as a complete premix, a fungicidal action is achieved that exceeds what would have been expected from an additive mixture of the individual components at comparable use rates. The surprisingly increased effects permit dosage rates of the individual components to be significantly reduced, thereby reducing the environmental loading of turfgrass. Such reduction in chemical exposure is increasingly important to golf course superintendants, lawn care operators, and turfgrass managers.

For snow mold treatment, once again the dosage required to achieve 4 month control or longer beneath snow cover is reduced compared to traditional treatments. At the same time, other properties sought by end-users are considerably improved in comparison with prior two-way premixes or tank-mixes.

With the present quaternary combination, turfgrass disease is controlled reliably whether or not applied prophylactically at the time of year when climate conditions favor disease or at the first sign of impending outbreak. Accuracy of application, speed of effect, residual control for the dosage applied, and flexibility of use are all improved. The present combination provides a most economical and simple-to-implement approach to turfgrass disease management.

Accordingly, in one aspect the present subject matter relates to a surprising, unique premix of four fungicides for improved turfgrass and horticulture treatment. In marked contrast with the mixing of individual fungicides at the spray tank, application of this embodiment of the present quaternary combination means users are 1) not faced with having the wrong fungicide on site, 2) employing the wrong ratio of one fungicide to the other, 3) needing to read a suite of individual labels on how to balance the variety of products safely and in compliance with EPA regulations, 4) mixing and matching fractions of an ounce per M on the spot, or 5) needing to wear protective aprons and safety shields for the more toxic components of a particular and oftentimes improvised tank-mix.

In this regard, when used as a premix the present mixture provides unexpectedly efficient protection from a broad spectrum of pathogens encountered in-season, while imparting extended control of snow mold (pink and gray) through winter without growth regulator effects that typically thin both warm- and cool-season grasses. In one embodiment, the present premix can be formulated in a single stable, highly-concentrated, dilutable product which is used in whole ounces per M and/or convenient 4 fl oz increments for the entire array of diseases, ensuring accurate and efficacious application.

The present subject matter thus provides a quaternary fungicide mixture comprising: (i) chlorothalonil, (ii) iprodione, (iii) thiophanate methyl, and (iv) tebuconazole, or an ester of any of the foregoing.

According to one aspect, the present subject matter provides a broad spectrum, stable, ready to dilute composition comprising this same quaternary fungicide mixture. This composition can be provided in an ultra-high concentration that preferably provides a multi-site mode of action.

In an alternative aspect, the present subject matter also relates to a tank-mix of the same four fungicides that provides improved turfgrass and horticulture treatment. Since guidance can be provided regarding the ranges and/or ratios of amounts to use for each fungicide in the mixture, a tank-mix provides the advantage of being able to optimize the specific desired ratio at the point of use. Further, since the present quaternary combinations require lesser amounts of each fungicide to achieve a synergistic effect, the difficulties of working with the more toxic components can be reduced.

According to a further aspect, the present subject matter provides herein a method for controlling phytopathogenic fungal diseases of turfgrass or ornamental species, comprising contacting the fungi, the turfgrass or ornamental species, or soil containing the same, with an effective amount of the quaternary fungicide mixture or compositions described herein.

According to a further aspect, the present subject matter provides herein a method for controlling overwinter, spring, summer, or fall turfgrass or ornamental disease, comprising contacting turfgrass or ornamental species infected with overwinter, spring, summer, or fall turfgrass disease, or soil containing the same or infected with snow mold, with an effective amount of the quaternary fungicide mixture or compositions described herein.

According to still another aspect, the present subject matter provides herein a synergistic mixture of four fungicides in which the total response of an array of host pathogens against which the fungicide combination is targeted is unexpectedly greater than the sum of the response to the individual components.

DETAILED DESCRIPTION OF THE PRESENT SUBJECT MATTER

Definitions

Prior to setting forth the present subject matter in detail, it may be helpful to provide definitions of certain terms to be used herein. Unless defined otherwise, all technical and scientific terms used herein have the same meaning as is commonly understood by one of skill in the art to which this subject matter pertains.

As used herein, the phrase "agriculturally acceptable carrier" means carriers, which are known and accepted in the art for the formation of formulations for agricultural or horticultural use.

As used herein, the term "anti-crystallization" means an agriculturally acceptable material which include pyrrolidinone polymer, mineral earths such as silica gels, cellulose powders, kaolin, attaclay, bentonite, sodium carbonate and bicarbonate, milled synthetic materials, and products of vegetable origin, such as humic acid, vegetable oils and lecithins.

As used herein, the phrase "liquid carriers" means an agriculturally acceptable material which include water, alcohols such as methanol, cyclohexanol, and decanol, ethylene glycol, propylene and polypropylene glycol, N,N-dimethylformamide, dimethylsulfoxide, N-alkylpyrrolidone, aromatic hydrocarbons such as alkylbenzenes and alkylnaphthalenes, paraffins, fertilizers, for example, trace nutrients such as salts of manganese, boron and zinc, ammonium phosphate, ammonium nitrate, urea, oils of olive, castor, linseed, tung, sesame, corn, peanut, cotton-seed, soybean, rape-seed and coconut, fatty acid esters, ketones such as cyclohexanone, 2-heptanone, isophorone, and 4-hydroxy-4-methyl-2-pentanone, and the like.

As used herein, the term "mixture" or "combination" refers, but is not limited to, a combination in any physical form, e.g., blend, solution, alloy, or the like.

As used herein, the phrase "multiple mixture" means a combination of at least four active substances.

As used herein, the phrase "ready to dilute" means compositions which include all necessary ingredients and for which there is no need to add further excipients, such as an adjuvant.

As used herein, the term "surfactant" means an agriculturally acceptable material which imparts emulsifiability, stability, spreading, wetting, dispersibility or other surface-modifying properties. Examples of suitable surfactants include non-ionic, anionic, cationic and amphoteric types such as lignosulfonates, fatty acid sulfonates (e.g. sodium lauryl sulfonate), fatty acid taurates, phosphate esters such as phosphate esters of alcohol alkoxylates, phosphate esters of alkylphenol alkoxylates and phosphate esters of styrylphenol ethoxylates, polyalkoxyether sulfates, alkyl sulfosuccinates, condensates of sulfonated naphthalene and naphthalene derivatives with formaldehyde, condensates of naphthalene or of naphthalenesulfonic acid with phenol and formaldehyde, alkylarylsulfonates, ethoxylated alkylphenols and aryl phenols, polyalkylene glycols, sorbitol esters, alkyl polyglycosides, alkylene oxide block copolymers, and ethoxylated fatty alcohols.

As used herein, the phrase "ultra-high concentration" means active substances in amounts of at least 500 g per liter.

The term "a" or "an" as used herein includes the singular and the plural, unless specifically stated otherwise. Therefore, the terms "a," "an" or "at least one" can be used interchangeably in this application.

Throughout the application, descriptions of various embodiments use the term "comprising"; however, it will be understood by one of skill in the art, that in some specific instances, an embodiment can alternatively be described using the language "consisting essentially of" or "consisting of."

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques. In this regard, used of the term "about" herein specifically includes ±10% from the indicated values in the range. In addition, the endpoints of all ranges directed to the same component or property herein are inclusive of the endpoints, are independently combinable, and include all intermediate points and ranges.

All publications, patents and patent applications mentioned in this specification are herein incorporated in their entirety by reference into the specification, to the same extent as if each individual publication, patent or patent application was specifically and individually indicated to be incorporated herein by reference.

Quaternary Fungicidal Mixture

The present subject matter relates to a quaternary fungicide mixture comprising: (i) chlorothalonil, (ii) iprodione, (iii) thiophanate methyl, and (iv) tebuconazole, or an ester of any of the foregoing. This mixture provides enhanced control of diseases of grasses, such as turf or ornamental grass. The fungicide mixture may further result in a synergistic fungicidal activity depending upon the fungal disease against which the mixture is applied.

In an additional embodiment, the present subject matter relates to a synergistic quaternary mixture comprising: (i) chlorothalonil, (ii) iprodione, (iii) thiophanate methyl, and (iv) tebuconazole, or an ester of any of the foregoing.

In one embodiment, the weight ratio of active chlorothalonil in the mixture, a contact, multi-site fungicide, to the combined weight ratio of active iprodione+active thiophanate methyl+active tebuconazole in the mixture, is from about 1.1:1 to about 1.9:1, preferably 1.3 to 1.

In another embodiment, the weight ratio of active chlorothalonil to active tebuconazole, representing a SBI, in the mixture is from about 6.4:1 to about 14.5:1, preferably about 10 to 1.

In a further embodiment, the weight ratio of active iprodione, a fungicide that inhibits histidine kinase osmoregulation, to active thiophanate methyl, an inhibitor of beta-tubulin assembly in nuclear division, is from about 2:1 to about 1:2, preferably about 1 to 1.

In a further embodiment, the combined weight ratio of acropetal penetrants, such as active iprodione and thiophanate methyl in the mixture, to a SBI, such as tebuconazole, is from about 4:1 to about 10:1, preferably about 7.5 to 1.

In an embodiment of the present subject matter, a predetermined ratio of complementary contact, limited and/or fully systemic, and SBI fungicides provides protective and curative fungicidal action. Unexpectedly, this combination provides superior and broad-spectrum control at a far lower dosage of active ingredient per treatment than previously observed.

In a specific embodiment, the present mixtures contain 360 g/l of active chlorothalonil, 120 g/l of active iprodione, 120 g/l of active thiophanate methyl and 36 g/l of active tebuconazole. In another specific embodiment, the present mixtures contain 290 g/l of active chlorothalonil, 93 g/l of active iprodione, 93 g/l of active thiophanate methyl and 29 g/l of active tebuconazole.

In a further embodiment, the present subject matter relates to a fungicide composition comprising a mixture as described herein. This composition provides improved pesticidal activity, and may broaden the spectrum of fungal control at significantly lower dosages of the active ingredients to be used when compared to the use of such individual pesticides alone or in two- or three-way tank-mixtures.

According to another aspect, the present subject matter provides a broad spectrum, stable, ready to dilute composition comprising this same quaternary fungicide mixture. This composition can be provided in an ultra-high concentration, and will preferably provide a multi-site mode of action.

In particular, prior premixes containing chlorothalonil were limited to two- and three-way mixtures of fungicides whose total active ingredient was about 500 g/l or less and whose forms were physically incompatible in storage leading to erratic and imprecise dosing of the fungicides during subsequent dilution. In contrast, the present composition comprises about 260 to 425 g/l active chlorothalonil, about 65 to 155 g/l iprodione, about 80 to 145 g/l thiophanate methyl, and about 29 to 45 g/l tebuconazole as a water dilution of the composition. In another embodiment, the present compositions can comprise 360 g/l or 290 g/l chlorothalonil, 120 g/l or 93 g/l iprodione, 120 g/l or 93 g/l thiophanate methyl, and 36 g/l or 29 g/l tebuconazole.

In an embodiment, the present subject matter provides a composition comprising: (i) chlorothalonil, (ii) iprodione, (iii) thiophanate methyl, and (iv) tebuconazole, or an ester of any of the foregoing. These compositions may further comprise an agriculturally acceptable carrier.

In yet another embodiment, the present compositions can further comprise at least one additional component selected from the group consisting of surfactants, rheology modifiers, antisettling agents, antifoam agents, buffers, and liquid diluents. Other ingredients, such as wetting agents, adhesives, thickeners, binders, colorants such as phthalocyanine pigments, or antifreeze agents, may also be added to the composition consisting of the combination of the fungicides in order to increase the stability, density, appearance and ease-of-handling of the composition.

The present compositions may include additional crop protection agents, for example insecticides, acaricides, nematicides, safeners, or such preservatives as bacteriostats or bactericides. However, for the avoidance of doubt, it is understood that such additional crop protection agents are unnecessary to achieve the synergistic effects of the present mixtures and compositions. Accordingly, the present fungicidal compositions and fungicidal mixtures may be limited to those containing (i) chlorothalonil, (ii) iprodione, (iii) thiophanate methyl, and (iv) tebuconazole, or an ester of any of the foregoing as the only crop protection agents and/or fungicides present.

In one embodiment, the compositions presented herein are suspension concentrates. Liquid compositions, whether aqueous- or oil-based, eliminate the need to granulate or to control fines and static that increase handler exposure to dust. In an embodiment, the weight percentage of the combination of the four fungicides, i.e., the chlorothalonil, iprodione, thiophanate methyl, and tebuconazole, in the suspension concentrate (SC) formulations is about 35 to 65 wt. %, based on the total weight of the formulation. In a further embodiment, the SC formulations consist essentially of a) from 22% to 40.5% of chlorothalonil; b) from 5.6 to 18.2% of iprodione; c) from 5.6 to 18.2% of thiophanate methyl; and d) from 2.4% to 3.7% tebuconazole; wherein the total amount of chlorothalonil, iprodione, thiophanate methyl, and tebuconazole in the composition is greater than 500 grams per liter; and wherein all % are % by weight based upon the total weight of all components in the composition. In another embodiment, the weight percentage of the combination of the four active compounds in the SC formulations is about 50%, based on the total weight of the formulation.

In another specific embodiment, the weight percentage of the combination of the four active compounds is about 56-62 wt. %, more specifically 58 wt. %, based on the total weight of the formulation.

In another embodiment, the SC is prepared by mixing the components of the fungicide mixture with a nonionic surfactant, an anionic surfactant, and/or an anti-crystallization agent.

The present compositions can be concentrated compositions or prepared in advance by diluting such concentrates. Typical dilutions are from 10-27 liters of composition Ha$^{-1}$ applied in 400-1000 liters water Ha$^{-1}$.

In an embodiment, the present subject matter relates to a method for controlling phytopathogenic fungal diseases of turfgrass or ornamental vegetation/species comprising contacting the fungi or the turfgrass or ornamental vegetation/species, or soil containing the same, with an effective amount of a quaternary fungicide mixture comprising: (i) chlorothalonil, (ii) iprodione, (iii) thiophanate methyl, and (iv) tebuconazole, or an ester of any of the foregoing.

The multiple mixture of active substances can be diluted and applied in a customary manner, for example by watering (drenching), drip irrigation, spraying, and atomizing.

The methods described herein are contemplated for treating various turf and ornamental grass or other woody and herbaceous species by application of the described compositions. Turfgrass species that the described compositions can be used on include cool- and warm-season grasses such as but not limited to Bentgrasses, Bermudagrasses, Bluegrasses, Fescues, Ryegrasses, St. Augustine grasses, and Zoysia grasses or their mixtures, creeping bentgrass, colonial bentgrass, annual bluegrass, other *Poa* species of grasses, Bermuda grass, Rye grass, and other common grasses of golf courses, sport fields and sod farms.

In another embodiment, ornamental species that the described compositions can be used on include Herbaceous Bedding, Flowering plants such as Chrysanthemum, Poinsettia, Hydrangea, Tropical Foliage such as Dracaena, Woody Ornamentals such as Azalea Rhododendron, Hibiscus, Ligustrum, Evergreen Trees such as Blue Spruce and Fir, Deciduous Trees such as Ash, Maple, Oak and Walnut, Flowering trees such as Cherry, Crabapple, Mountain Ash and Pear, Woody Ornamental shade trees, Roses, Pyracantha and Ornamental nut and fruit trees.

The described compositions may be applied to healthy or diseased turfgrass or ornamental species. Prophylactic application to healthy turfgrass may be helpful in preventing turfgrass diseases. Application to turfgrass containing one or more turfgrass diseases is helpful in treating the one or more turfgrass diseases. The turf and ornamental grass diseases that the described compositions can treat include Anthracnose (Basal and Foliar), Dollar Spot; Copper Spot; Brown Patch, Yellow patch, Take-all patch and Zoysia Patch; Red Thread; Gray Leaf Spot; Summer Patch; *Fusarium* Blight; Necrotic Ring Spot and Spring Dead Spot; Stripe Smut; Gray and Pink Snow Mold; *Fusarium* patch; Ascochyta Blight; Black spot; *Botrytis*; Brown Rot, *Colletotrichum; Cercospora* Leaf Spot, *Corynespora* Leaf Spot, *Didymellina* Leaf Spot, *Diplodia* Tip Blight, *Ovulinia, Entomosporium* Leaf Spot, *Fusicaladium* Leaf Scab, *Phomopsis* Blight, Powdery Mildew, Rust Diseases, *Ramularia* Leaf Spot, Scab, *Septoria* Leaf Spot and *Alternaria*; Black Spot of Rose; Brown Rot and Blight; *Fusicladium; Venturia* Leaf Scabs; Leaf Spots and Blights; Rust Diseases; Pine Tip Blights, *Sphaeropsis sapinea, Diplodia pinea*; Twig Blights, Cankers, and Diebacks, Diaporthe, *Kabatina* Phoma, and *Phomopsis*.

In yet another embodiment the phytopathogenic fungi which affect turfgrass and ornamental species treatable by the present mixtures and compositions include: *Colletotrichum cereale; Sclerotinia homoeocarpa; Sclerotium rolfsii; Gloeocercospora sorghi; Rhizoctonia solani; Laetisaria fuciformis; Microdochium nivale; Pyricularia grisea; Magnaporthe poae; Fusarium roseum; Leptosphaeria korrae; Ustilago striiformis; Typhula* spp; Gray Mold, *Diplodia pinea; Diplocarpon rosae; Monilinia, Sclerotinia, Whetzellinia; Aschyta, Blumeriella, Botrytis, Cercospora, Coccomyces, Corynespora, Curvularia, Didymellina, Entomosporium, Fabraea, Fusarium, Ramularia, Rhizoctonia, Marssoninia, Mycosphaerella, Myrothecium, Phoma, Physalaspora, Schizothyrium, Septoria, Sphaceloma, Puccinia, Gymnosporangium,* and *Uromyces*.

As described above, the present subject matter relates to a synergistic mixture or composition of the four specific enumerated fungicides. A synergistic effect exists wherever the action of a combination of active substances exceeds the total of the action of the active substances when applied individually. Therefore, a synergistically effective amount (or an effective amount of a synergistic mixture, composition, or combination) as discussed herein is an amount that exhibits greater fungicidal activity than the sum of the individual components at comparable rates of treatment.

In the context of the present subject matter, the term "synergy" is as defined by S. R. Colby in an article entitled "Calculation of the synergistic and antagonistic responses of herbicide combinations" published in the journal *Weeds*, 1967, 15, p. 20-22, incorporated herein by reference in its entirety. The action expected for a given combination of four active components can be calculated as follows:

$$E = X + Y + Z + W - \frac{XY + XZ + XW + YZ + YW + ZW}{100} + \frac{XYZ + XYW + XZW + YZW}{10000} - \frac{XYZW}{1000000}$$

in which E represents the expected percentage of fungicidal control (percent inhibition) for the multiple mixture of fungicides at defined doses (for example equal to x, y, z and w, respectively). X is the percentage of fungicide control observed by chlorothalonil at a defined dose (equal to x). Y is the percentage of fungicide control observed by iprodione at a defined dose (equal to y). Z is the percentage of fungicide control observed by thiophanate methyl at a defined dose (equal to z). W is the percentage of fungicide control observed by tebuconazole at a defined dose (equal to w). Here, efficacy or percent inhibition is determined in %. 0% means efficacy that corresponds to the Control, i.e., as if no treatment had been applied. Whereas, a percent inhibition of 100% means that no infection is observed. When the percent inhibition observed for the combination is greater than E, there is a synergistic effect. When the percent inhibition observed for the combination is equal to E, there is an additive effect and wherein the percent inhibition observed for the combination is lower than E, there is an antagonistic effect.

In the Colby model, one can transform its use of "percent inhibition" (or control) to "percent-of-untreated Control" to solve for $E_1$ rather than E and simplify the equation:

$$E_1 = \left[\frac{(X_1)(Y_1)(Z_1)(W_1)}{1000000}\right]$$

where $E_1 = 100 - E$ (conversely, solving for E, $100 - E_1 = E$), $X_1 = 100 - X$, $Y_1 = 100 - Y$, $Z_1 = 100 - Z$, and $W_1 = 100 - W$.

Although many combinations of fungicides have been studied and evaluated by means of the Colby Index, it is quite clear by modeling such synthetic expressions of synergy that the addition of a third, or even fourth, active ingredient to the premix may encounter the Point of Diminishing Returns caused by correction factors for 3- and 4-way interactions that offset the increase in E (or decrease in $E_1$). In marked contrast, the present subject matter has shown an expansive effect and performance boost so great that differences between the observed and expected values computed according to Colby can best be used as a descriptive statistic confirming the quaternary fungicidal mixture's obvious effect.

The following examples illustrate the practice of the present subject matter in some of its embodiments, but should not be construed as limiting the scope of the present subject matter. Other embodiments will be apparent to one skilled in the art from consideration of the specification and examples. It is intended that the specification, including the examples, is considered exemplary only without limiting the scope and spirit of the present subject matter.

EXAMPLES

Formulation Example

The synergistic fungicidal suspension concentrate formulations used in the below described experiments are set forth in Tables 1 and 2 below:

TABLE 1

Suspension concentrate

| Ingredient | g/L |
|---|---|
| Chlorothalonil | 370 |
| Iprodione | 121 |
| Thiophanate methyl | 121 |
| Tebuconazole | 37 |
| Surfactant | 55 |
| Other ingredients | 76 |
| Water | 490 |

TABLE 2

Suspension concentrate

| Ingredient | g/L |
|---|---|
| Chlorothalonil | 269.9 |
| Iprodione | 70 |
| Thiophanate methyl | 139 |
| Tebuconazole | 33.6 |
| Surfactant | 51.6 |
| Other ingredients | 69.7 |
| Water | 566.5 |

Comparative Test Results

A field study was conducted to identify which combinations would maintain or improve Turf Quality (TQ) and prevent or cure crown, basal or foliar pathogens such as dollar spot. Each solo treatment, 2-way (Pair), 3-way (Triad), and the present quaternary fungicidal mixture was applied bi-weekly beginning Jul. 1, 2013 prior to any evidence of decline in TQ or appearance of disease. Experimental plots were laid out in a Randomized Complete Block design.

The dosage of each fungicidal active substance was held constant regardless of whether it appeared alone or in combination with other fungicides in order to quantify synergy according to the Colby formula. The quaternary mixture of the present subject matter was applied at the lowest rate specified herein, about 5.5 lb active substance per acre. Applications were made to replicate plots of creeping bentgrass (*Agrostis stolonifera*), each measuring 3 ft×5 ft. The turf was mowed as needed to maintain standard fairway height (blade length less than 0.5"). Four applications were made at 14 day re-treatment intervals, which is a conventional treatment schedule at the time of year when outbreaks of turfgrass disease occur reliably in the mid-Atlantic region (Greenville, Del.).

The mix rate and volume of dilute spray applied to each plot was held constant. A $CO_2$ backpack sprayer outfitted with TeeJet AI9504E flat fan nozzle delivered a water dilution of each treatment at the use rate of 43.5 gallons per acre (407 liters Ha$^{-1}$) and 35 psi (0.375 gallons per minute).

Plots were evaluated and disease or cause of lesion identified 15 days after the final scheduled application, which was made on 12 August. At that time researchers rated each plot's TQ, the incidence of disease and its severity. Percent disease ratings were calculated on the basis of the percent of area of each plot showing symptoms of a disease, primarily dollar spot. Turf quality and color ratings are typically used as an indicator of the health of the turfgrass. Turf quality is scored on an ordinal scale from 1-9, where plots rated 8 and higher are considered ideal for color, uniformity and density, around 6.5 and above is considered acceptable, and ratings under 6 unacceptable for turfgrass disease and/or turf quality.

Disease pressure evidenced by the untreated control ratings was considered severe. Six untreated control plots averaged 40% incidence, primarily due to a continuous increase in dollar spot pressure over time. By the end of the trial, TQ of the untreated plots declined to a low level, where leaf dieback, bleaching and lesions rated an average TQ of 4.2. Turf quality of plots treated with each active substance alone at these dosages was poor, averaging 3.9.

Table 3 is arranged in groups to facilitate comparison of the six plots to which the present subject matter was applied with other treatments blocked according to whether they were step-wise additions of 1) iprodione, thiophanate methyl and/or tebuconazole to comprise chlorothalonil-based pairs or triads; 2) iprodione, thiophanate methyl and/or chlorothalonil to comprise tebuconazole-based pairs or triads; or 3) remaining pairs or triads formed of iprodione or thiophanate methyl. At trial's end, these latter two active substances, applied alone, had percent inhibition and TQ no better than the untreated control.

Index rose by 41 points as well. Finally, the addition of tebuconazole to Triad #1, comprising the quaternary mixture, improved TQ by 2.8, to ideal, almost doubled percent inhibition and increased Colby Index by 25 points. Thus, applying the multiple mixture every 14 days at the low rate of about 5.5 lb of active substances per acre produced virtually disease-free plots for the entire summer and achieved a TQ rated ideal.

In accordance with the present subject matter, step-wise addition of any fourth component, regardless of whether it was a protectant active, an acropetal penetrant, or a true systemic, accelerated disease control beyond the improvement obtained from adding any third component to any Pair (to comprise a Triad) and improved TQ as well. Significant improvement in TQ did not occur by adding any third component to any Pair nor upon pairing individual components.

The high degree of synergistic effect observed in the quaternary mixture did not appear to result from extending the range of activity or to be caused by any single compound's inclusion in a pair or triad since a similar synergistic effect was observed whenever any fourth compound was added to the other three at the ratios recited herein. In Table 4, there is acceleration of synergistic effect caused by the addition of a fourth active substance to a triad. The average gain to Colby Index as a result of step-wise addition of any fourth active substance to comprise the quaternary mixture from a triad was 24.1 points (a standard deviation of 12.7 points). The average rating of TQ improved 2.4 points. The average increase to Colby Index as a result of adding a third compound to any Pair was about half as much (12.5 points, with a standard deviation of 12.2) and average TQ barely improved.

TABLE 3

| Treatment Code | Chlorothalonil (LBai/A) | Iprodione (LBai/A) | Thiophanate methyl (LBai/A) | Tebuconazole (LBai/A) | Percent Inhibition | Turf Quality | Colby Index |
| --- | --- | --- | --- | --- | --- | --- | --- |
| Chlorothalonil | 3.1 | — | — | — | 15.8 | 4.3 | — |
| Iprodione | — | 1.03 | — | — | 5.8 | 4.0 | — |
| Thio methyl | — | — | 1.03 | — | 0 | 3.3 | — |
| Tebuconazole | — | — | — | 0.31 | 19.3 | 4.0 | — |
| Pair #1 | 3.1 | — | 1.03 | — | 20.8 | 4.7 | 5.0 |
| Pair #2 | 3.1 | 1.03 | — | — | 69.3 | 5.3 | 48.7 |
| Triad #1 | 3.1 | 1.03 | 1.03 | — | 54.3 | 5.2 | 33.7 |
| Triad #2 | 3.1 | 1.03 | — | 0.31 | 83.3 | 6.7 | 47.4 |
| Quaternary | 3.1 | 1.03 | 1.03 | 0.31 | 95.0 | 8.0 | 59.1 |
| Pair #3 | 3.1 | — | — | 0.31 | 59.3 | 5.8 | 27.3 |
| Pair #4 | — | — | 1.03 | 0.31 | 38.3 | 5.0 | 19.0 |
| Triad #3 | 3.1 | — | 1.03 | 0.31 | 50.0 | 5.0 | 18.0 |
| Triad #4 | — | 1.03 | 1.03 | 0.31 | 65.0 | 5.5 | 41.1 |
| Pair #5 | — | 1.03 | — | 0.31 | 55.8 | 5.5 | 31.9 |
| Pair #6 | — | 1.03 | 1.03 | — | 9.3 | 4.7 | 3.5 |
| Quaternary | 3.1 | 1.03 | 1.03 | 0.31 | 95.0 | 8.0 | 59.1 |

Only once did the addition of thiophanate methyl markedly improve TQ; when it was included in the top-performing quaternary fungicidal mixture (Triad #2 plus thiophanate methyl). The addition of thiophanate methyl to Pair #5 to comprise Triad #4 offered no improvement in TQ and only 9 points in the Colby Index. However, step-wise addition of chlorothalonil to Triad #4, to comprise the present quaternary mixture, improved TQ from unacceptable to ideal (5.5 to 8), and raised synergy 18 points. Similarly, adding iprodione to Triad #3 to comprise the quaternary mixture raised TQ 3 points from an unacceptable score of 5, achieved a percent inhibition twice that of the triad (95% vs. 50%), and its Colby

TABLE 4

Gain to Colby Index and Turf Quality if active substance added

|  | Colby Gain | TQ Gain |
| --- | --- | --- |
| To Pairs to form Triads: | | |
| Average of addition of Chlorothalonil to Pairs #4, #5, and #6 | 14.9 | 0.6 |
| Average of addition of Iprodione to Pairs #1, #3, and #4 | 23.6 | 0.6 |

TABLE 4-continued

Gain to Colby Index and Turf Quality if active substance added

|  | Colby Gain | TQ Gain |
|---|---|---|
| Average of addition of Thiophanate methyl to Pairs #2, #3, and #5 | −5.0 | −0.3 |
| Average of addition of Tebuconazole to Pairs #1, #2, and #6 | 16.4 | 0.8 |
| Average Gain | 12.5 | 0.4 |
| To Triads to form Quaternary Fungicidal Mixture: | | |
| Addition of Chlorothalonil to Triad #4 | 18.0 | 2.5 |
| Addition of Iprodione to Triad #3 | 41.1 | 3.0 |
| Addition of Thiophanate methyl to Triad #2 | 11.7 | 1.3 |
| Addition of Tebuconazole to Triad #1 | 25.4 | 2.8 |
| Average Gain | 24.1 | 2.4 |

The reference pathogen evaluated was dollar spot, *Sclerotinia homeocarpa*, a pathogen well known to have developed resistance to many classes of fungicides, in particular the benzimidazoles of which thiophanate methyl is a member. In fact, treatment by thiophanate methyl alone appeared to flare the severity of dollar spot since its individual plots had significantly lower ratings than those of the untreated Control. Its inclusion in a Pair or Triad contributed little or no improvement in TQ. To illustrate, for Pairs #2 or #3, the inclusion of thiophanate methyl to comprise Triad #1 or Triad #3, respectively, materially reduced the percent inhibition, Colby Index and TQ of each Triad compared to each Pair without thiophanate methyl. The addition of thiophanate methyl to pairs to form triads caused an average loss in Colby Index of 5 points and 0.3 in scoring TQ. Yet, in the presence of the complete complement of fungicides contained in the quaternary mixture, thiophanate methyl unexpectedly contributed to improved indices of efficacy (about 12 points) and turfgrass health (plots improved to an ideal quality of 8 from a marginally acceptable 6.7).

Chlorothalonil 720 SC recommends 7.2-11.25 lb active chlorothalonil per acre to achieve only 7-14 day control, while the present compositions achieve longer control (14-21 days) with just 3-4 lb active chlorothalonil per acre.

Iprodione 2SC recommends 2.72-5.44 lb active iprodione per acre to achieve 14-21 day control, while the present compositions allow users to apply 1-1.36 lb active iprodione per acre for equal length of control.

Thiophanate methyl 4.5 SC recommends 5.35-8.1 lb active thiophanate methyl at a 14-day re-treatment interval, while the present compositions allow users to apply 1-1.36 lb active thiophanate methyl per acre to achieve longer control.

Torque™ 3.6 SC Fungicide recommends 0.74 lb active tebuconazole per acre to achieve 21-28 day control, while the present compositions enable users to apply just 0.3-0.4 lb active tebuconazole per acre for similar duration of control.

Consequently, attempting to recreate the synergistic effect of the quaternary fungicidal mixture by tank-mixing the aforementioned individual products at the midpoint rate specified by each of those labels would mean applying 20.8 lb of active ingredient per acre for no better or longer control than was obtained with about 5.5 lb active ingredient of the present quaternary mixture at the ratios specified in the present subject matter.

Typical use rates per acre of turfgrass treated with quaternary fungicidal mixture will range from about 5.5 lb active ingredient per acre for prophylactic control with two week re-treatment intervals to no more than 14.5 lb active ingredient per acre in a single application for programs designed to suppress or control Pink and Gray snow mold for 4 months or longer.

While the present subject matter has been shown and described with reference to preferred embodiments thereof, it will be understood by those skilled in the art that many alternatives, modifications and variations may be made thereto without departing from the spirit and scope thereof. Accordingly, it is intended to embrace all such alternatives, modifications, and variations that fall within the spirit and broad scope of the appended claims.

We claim:

1. A quaternary fungicide mixture comprising:
   a) from 22% to 40.5% of chlorothalonil;
   b) from 5.6% to 18.2% of iprodione;
   c) from 5.6% to 18.2% of thiophanate methyl; and
   d) from 2.4% to 3.7% tebuconazole;
   wherein the total amount of chlorothalonil, iprodione, thiophanate methyl, and tebuconazole in the composition is greater than 500 grams per liter; wherein all % are % by weight based upon the total weight of all components in the composition, and wherein the mixture exhibits synergistic effects.

2. The mixture of claim 1, comprising about (i) 290 g/l of chlorothalonil, (ii) 93 g/l of iprodione, (iii) 93 g/l of thiophanate methyl, and (iv) 29 g/l of tebuconazole.

3. The mixture of claim 1, comprising about (i) 360 g/l of chlorothalonil, (ii) 120 g/l of iprodione, (iii) 120 g/l of thiophanate methyl, and (iv) 36 g/l of tebuconazole.

4. A broad spectrum, stable, ready to dilute composition comprising: the mixture of claim 1, wherein the composition is formed in a ready to dilute form and exhibits synergistic effects.

5. The composition of claim 4, further comprising an agriculturally acceptable carrier.

6. The composition of claim 4, wherein the composition provides a multi-site mode of action and is formulated at an ultra-high concentration.

7. The composition of claim 4, wherein the composition is a suspension concentrate.

8. The composition of claim 7, wherein the chlorothalonil, iprodione, thiophanate methyl, and tebuconazole have a weight percent combination of about 35 to about 65 wt. % in the suspension concentrate.

9. The composition of claim 1, wherein the composition further comprises at least one additional component selected from the group consisting of surfactants, rheology modifiers, antisettling agents, antifoam agents, buffers, and liquid diluents.

10. A method for controlling phytopathogenic fungal diseases of turfgrass or ornamental species, comprising contacting the fungi or the turfgrass or ornamental species, or soil containing the same, with an effective amount of the mixture according to claim 1.

11. A method for controlling phytopathogenic fungal diseases of turfgrass or ornamental plants, comprising contacting the fungi or the turfgrass or ornamental plants, or soil containing the same, with an effective amount of the mixture according to claim 1, wherein the combination of chlorothalonil, iprodione, thiophanate methyl, and tebuconazole ranges from about 5.5 lb to about 14.5 lb per acre (lb/acre) when said mixture is administered to said soil, turfgrass, or ornamental plants.

12. A method for controlling phytopathogenic fungal diseases of turfgrass or ornamental species, comprising contacting the fungi or the turfgrass or ornamental species, or soil containing the same, with an effective amount of the mixture according to claim 4.

* * * * *